(12) United States Patent
Zhou

(10) Patent No.: US 6,216,531 B1
(45) Date of Patent: Apr. 17, 2001

(54) TESTING TOOL ADAPTER

(75) Inventor: Joe Q. X. Zhou, Waterloo (CA)

(73) Assignee: Flexible Products Company, Marietta, GA (US)

( * ) Notice: Subject to any disclaimer, the term of this patent is extended or adjusted under 35 U.S.C. 154(b) by 0 days.

(21) Appl. No.: 09/450,956

(22) Filed: Nov. 30, 1999

(51) Int. Cl.⁷ .................................................. G01N 19/04

(52) U.S. Cl. ........................................................ 73/150 A

(58) Field of Search ............................ 73/856, 827, 830, 73/150 R, 150 A, 159

(56) References Cited

U.S. PATENT DOCUMENTS

| | | | |
|---|---|---|---|
| 3,788,135 | * | 1/1974 | Hammond, Jr. ........................ 374/15 |
| 4,010,641 | * | 3/1977 | Krieger, Jr. .......................... 73/150 A |
| 4,041,806 | * | 8/1977 | Klar ...................................... 73/159 |
| 4,612,805 | * | 9/1986 | Bruce et al. ........................ 73/150 A |

OTHER PUBLICATIONS

ASTM C557-93a—Specification for Adhesives for Fastening Gypsum Wallboard to Wood Framing, Published 2/1994.
ASTM D905-94—Method for Strength Properties of Adhesive Bonds in Shear by Compression Loading, Published 8/1994.
ASTM D3498-93—Specification for Adhesives for Field-Gluing Plywood to Lumber Framing for Floor Systems, Published 2/1994.

* cited by examiner

*Primary Examiner*—Max Noori
(74) *Attorney, Agent, or Firm*—Vedder Price Kaufman & Kammholz

(57) ABSTRACT

An adapter for a testing too for use in the testing of shear strength of an adhesive as applied to a test specimen has a structure that permits it to be used on testing machines either in a tension or in a compression mode. The testing tool includes a pair of coacting force blocks which slidably engage each other and move, relative to each other. Each such force block has a central opening into which a test specimen may be inserted. The openings in each of the force blocks engage a different one of the two test coupons that make up a testing specimen. The force blocks further have bearing surfaces that oppose each other so that they may engage the like opposing ends of the test specimen.

15 Claims, 4 Drawing Sheets

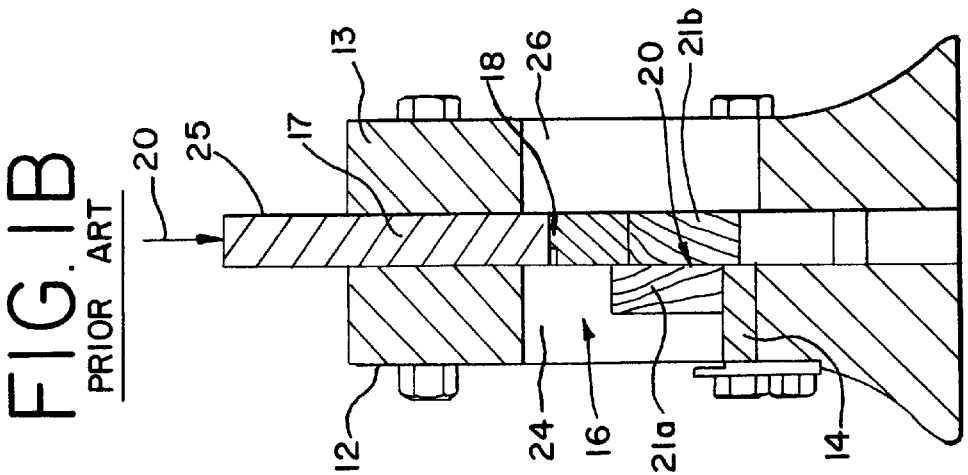
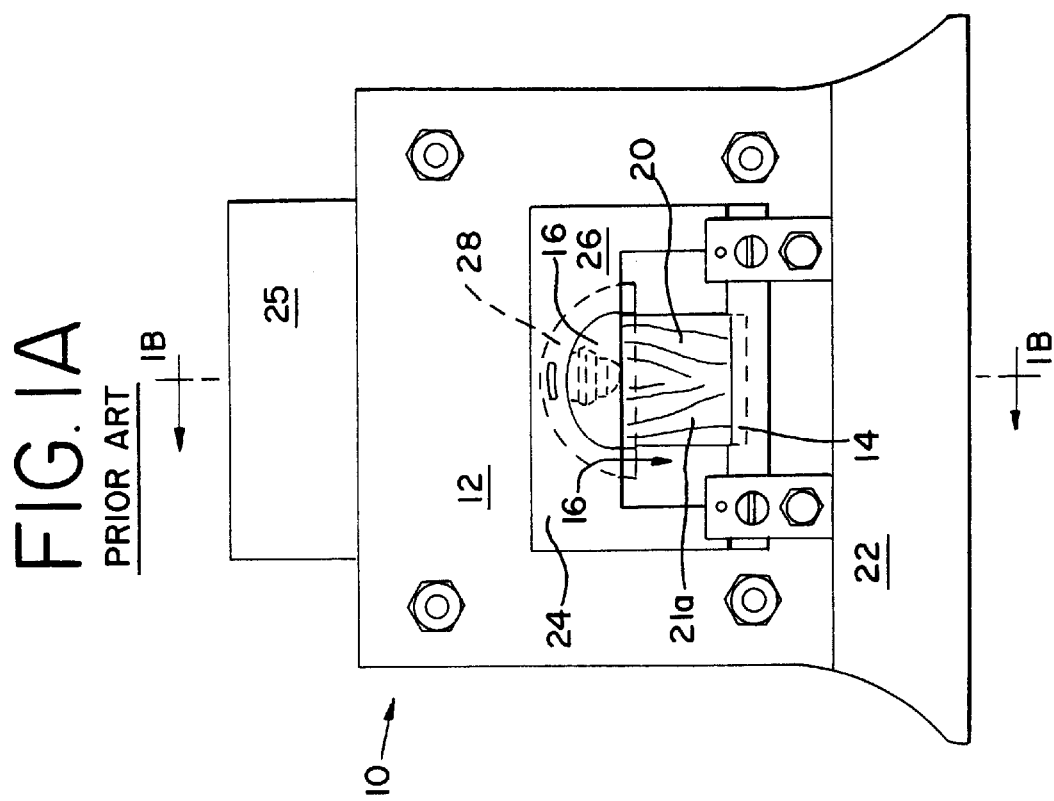

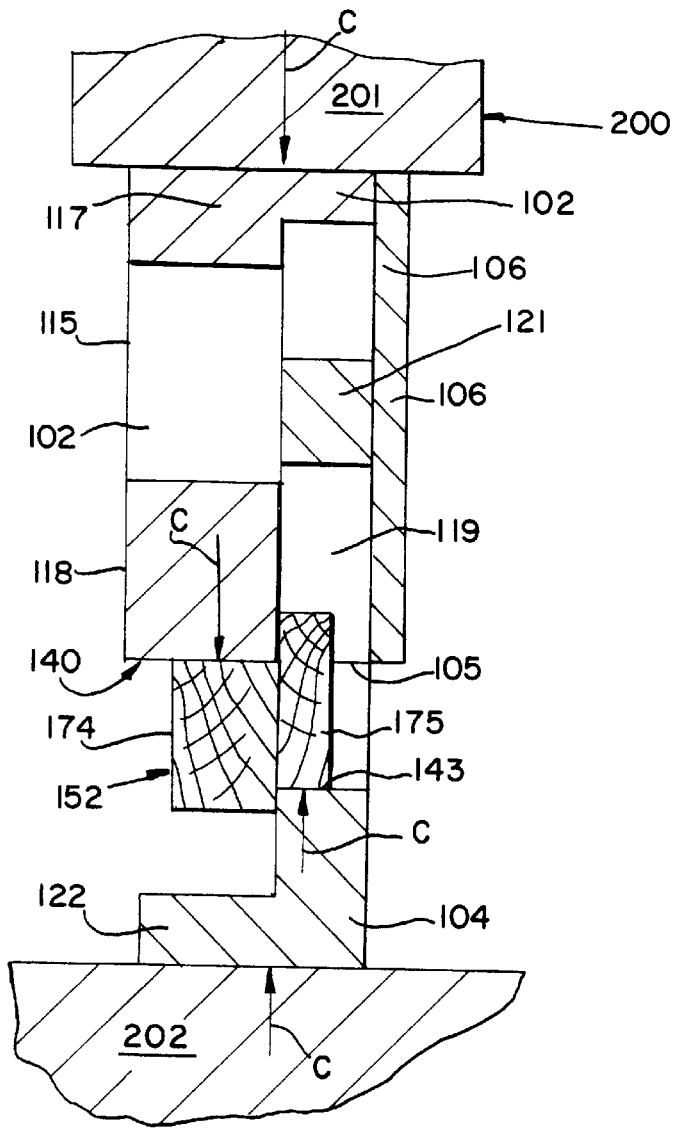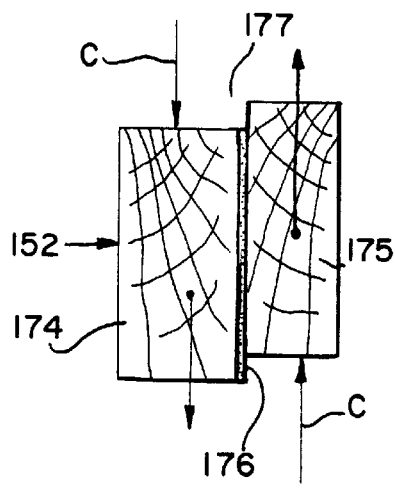

TESTING TOOL ADAPTER

BACKGROUND OF THE INVENTION

This invention relates generally to testing tools, and more particularly, to testing tool adapters for shear testing of adhesives used in securing wooden flooring to structural members and in securing gypsum-based wallboard to framing.

The American Society for Testing and Materials (ASTM) has developed testing standards for shear testing. Two of the testing standards are C 557-93a—Standard Specification for Adhesives for Fastening Gypsum Wallboard to Wood Framing (hereinafter ASTM C 557) and D 3498-93—Standard Specification for Adhesives for Field-Gluing Plywood to Lumber Framing for Floor Systems (hereinafter ASTM D 3498). In these two standards, ASTM specifies a protocol as to how a shear test should be performed. ASTM sets forth in these standards, the types of materials to be used, the starting conditions of the test, the duration of the test, the manner in which the test is conducted, and the minimum requirements for passing the test. Additionally, ASTM recommends a test method and device which may be used to perform the shear tests in D 905-94—Standard Test Method for Strength Properties of Adhesive Bonds in Shear by Compression Loading (hereinafter ASTM D 905). ASTM D 905 is herein incorporated by reference.

This known testing machine has significant disadvantages. Its structure limits its use to only a compression testing machine, and not a tension testing machine. The time involved to change test specimens is long. When initially positioning the specimen, it is necessarily preloaded with the weight of the blade. The prior art machine is without a mechanism to correct the shear test results for the weight of the blade. Indeed, specification D 905-94 indicates that many factors will bias the measurement obtained with the testing tool described therein, such as the design of the shear strength testing tool.

Another problem is that the prior art testing tool is made of steel. The machine was deliberately constructed out of steel because the design required the strength of the steel in order to have the machine sustain the forces applied to it. However, the use of steel causes significant problems. The weight of the steel that aided in the shear test causes operator fatigue problems because the operator must manually lift the heavy blade while positioning the test specimen. Additionally, the heavy blade frequently is dropped by the operator falling on the operator's hand or on the test specimen—potentially ruining the specimen because of the impact loading. This process of manually lifting the blade, and positioning the specimen is time-consuming. Additionally, the cost of manufacturing this testing device in steel is high. Different shear testing machines are required under ASTM C 557 and D 3498.

As such, a need currently exists for a shear testing device of universal utility in that it can be used in both compression and tension testing modes, and which is safer and easier to use, less expensive to construct and operate, and lest likely to exhibit a testing bias wherein the test specimens can be of varying size without changing the adapter, and can be operated in a tension or compression force-producing setting.

The present invention recognizes and addresses the foregoing disadvantages, and other prior art constructions.

SUMMARY OF THE INVENTION

Accordingly, it is a general object of the present invention to provide a new and improved shear testing machine adapter It is another object of the present invention to provide a testing adapter that can be used to carry out the tests set forth in either ASTM C 557 and ASTM D 3498 shear testing specifications.

It is still another object of the present invention to design a testing device to test the shear strength of an adhesive using either a compression or tension mode wherein the testing specimen is firmly held so that the forces applied to the testing specimen are directly applied to testing specimen.

A further object of the invention is to provide a safe, easy and quick to use shear testing adapter.

Yet another object of the invention is to provide a shear testing adapter for a variety of testing specimen sizes.

Still another object of the invention is to provide a lower cost testing tool.

These and other objects of the present invention are achieved by providing a shear testing tool that can be easily connected to an Instron testing machine for testing the shear strength of adhesives bonding together gypsum wallboard to wood framing and wood flooring to wood framing.

The present invention accomplishes these objects through its unique and novel structure. In accordance with the principles of the present invention and as exemplified by a first embodiment of the invention, a testing tool is provided having two force-imposing blocks. One block is held stationary by the testing machine, while the other block is made movable by connecting it to the moving element of the testing machine. One of the blocks can slide within a cavity of the first block. This second block is held in the cavity by means of a retaining frame and is slidable thereon under controlled effort such as by the drive member on an Instron testing machine. Each of the two blocks has an opening formed therein and which lie adjacent to each other so that a bifurcated test specimen opening, or window, is formed having at least one pair of opposing bearing surfaces on which opposite ends of the test specimen may be placed so the test specimen experiences a testing force.

In a second embodiment of the invention, the movable testing block has a moveable mounting plate formed thereon that is capable of movement from side-to-side within the testing block. This movement is close to a pivoting, or rocking movement, and permits the testing force to be uniformly exerted on test specimens that may have less than perfect edges.

These and other objects, features, and advantages of the present invention will be clearly understood through a consideration of the following detailed description.

BRIEF DESCRIPTION OF THE DRAWINGS

In the course of the description, reference will be made to the attached drawings in which:

FIG. 1A is an elevational view of a prior art shear testing device that is described and recommended in ASTM Standard D 905-94;

FIG. 1B is a cross-sectional view of the testing device of FIG. 1A taken along lines A—A thereof;

FIG. 5A is a cross-sectional elevational view of the testing tool of FIG. 2 shown in place within a testing machine and with a test specimen in place thereon, illustrating the operation of the testing tool in a compression mode;

FIG. 5B is a schematic diagram of the forces exerted on the test specimen when in a compression mode as shown in FIG. 5A;

DESCRIPTION OF THE INVENTION

Figure 4:
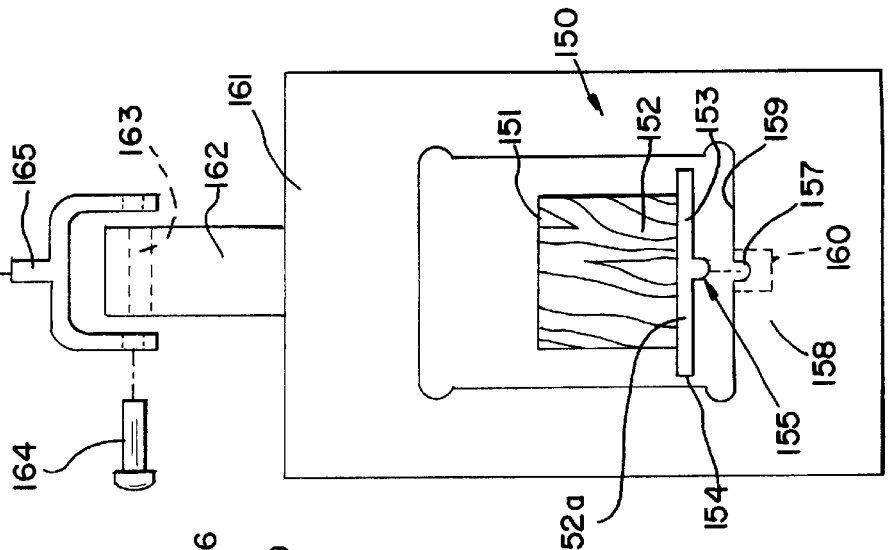
FIG. 4 is a front elevational view of a second embodiment of a testing tool constructed in accordance with the principles of the present invention, the embodiment having a moveable member operatively connected to its movable block.

Testing machines, such as an Instron testing machine, are mechanical systems that apply a load to test specimens. Instron machines can perform load-elongation that result in stress v. strain curve tests which involve loading forces from a few ounces to over a hundred-thousand pounds. Such machines have jaws that can grip specimens ranging from delicate fibers to high-strength metals or composites. In testing, the machines permit the development of a stress v. strain curve, or graph, of the material. Measurement of the stresses and strains may be accomplished by the use of highly sensitive load and strain transducers that create an electrical signal that is proportional to the applied stress or strain. The electrical signal is measured, digitized and then processed for display, analysis and report of stress, strain and other computed material characteristics.

In order to measure shear strength of a material or a substance using an Instron machine, an adapter must used. Because of the nature of shear strength, the adapter is placed offset from the Instron load head so that the load exerted on the test specimen comes from a pair of forces acting at a predetermined distance from the item or substance, or alternatively a moment. The force or moment is measured and calculated so that the results may be compared to the appropriate ASTM standards. The Instron machine can load test specimens hermaphroditically in either tension or compression.

The ASTM D 905 specifies a tool for testing shear shown in FIGS. 1A and 1B. The shear testing tool is shown generally at 10 and has two members 12, 13 which are disposed generally parallel to each other and connected to a supporting base 22 with a large opening 16 extending through both members 12, 13 and wherein the opening 16 is defined on its four sides by the members 12, 13. The members 12, 13 are rigid structures that create a perimeter for two openings 24, 26 formed in each of them, which cooperatively define the overall opening 16 of the testing tool 10.

The members 12, 13 are connected to the base 22 and are spaced apart from each other so that a testing blade 25 may be positioned between the members 12, 13 in a manner such that the blade 25 may slide within the intervening space. The testing blade 25 is operable between two positions. In its first position, the testing blade 25 extends into the tool opening 16 and completely between members 12 and 13 so that their associated openings 24, 26 do not communicate with each other. In its second position, the testing blade 25 is lifted upward to an extent that it permits at least partial communication between openings 24, 26. The testing blade 25 is a heavy piece of metal so that compressive forces 20 applied to the testing tool 10 are transferred through the testing blade 25 to the test specimen 18 without damaging the testing blade 25.

A self-adjusting bearing 18 is connected to the testing blade 25 by using a swivel mount 28. This bearing 18 is approximately the width of testing blade 25 so that it and the swivel mount 28 may move between the members 12, 13. The bearing 18 has a generally semi-circular configuration with an interior concave surface into which a test specimen, or coupon may be placed. The testing specimen 20 fits into the self-adjusting bearing 18 so that generally even pressure is transmitted from the blade 25 through self-adjusting bearing 18 to the test specimen 20.

The test specimen 20 is as described in ASTM 905 and 3498, and is essentially formed from two blocks 21a, 21b of wood or other material with an adhesive 21c bonding the two blocks together along a common interface. The first block 21a rests on a test stand 14 that is connected to the tool base 22, while the second block 21b fits into the self-adjusting bearing 18.

In operation, the testing tool 10 must be loaded manually with test specimens 20. Typically, one person does this, and this act may lead to a dangerous, and inefficient situation. The testing blade 25 is heavy for a one-handed operation, and it is typically lifted by the user with one hand so that the two member openings 24 and 26 at least partial communicate with each other and create a large opening 16 for use with a test specimen 20. With the other hand, the operator places the test specimen 20 on a test stand 14. The test specimen 20 must be carefully positioned so that the bearing 18 securely grips the second block 21b, but does not grip the first block 21a or it may adversely affect the results obtained in testing the specimen 20. The second block 21b must also not rest or contact the test stand 14 in order to obtain accurate results.

The first block 21a also needs to solidly rest on the test stand 14 while not being gripped by the self-adjusting bearing 18. In the operation process of this testing tool 10, the operator's hand holding the heavy blade 25 may lose its grip and drop the testing blade 25, leading to a likelihood that the operator's other hand may become hurt, if it is in the opening 16 of the tool 10. If the blade 25 drops on to the test specimen, the premature loading from the impact will cause errors in the measured results.

Figure 2:
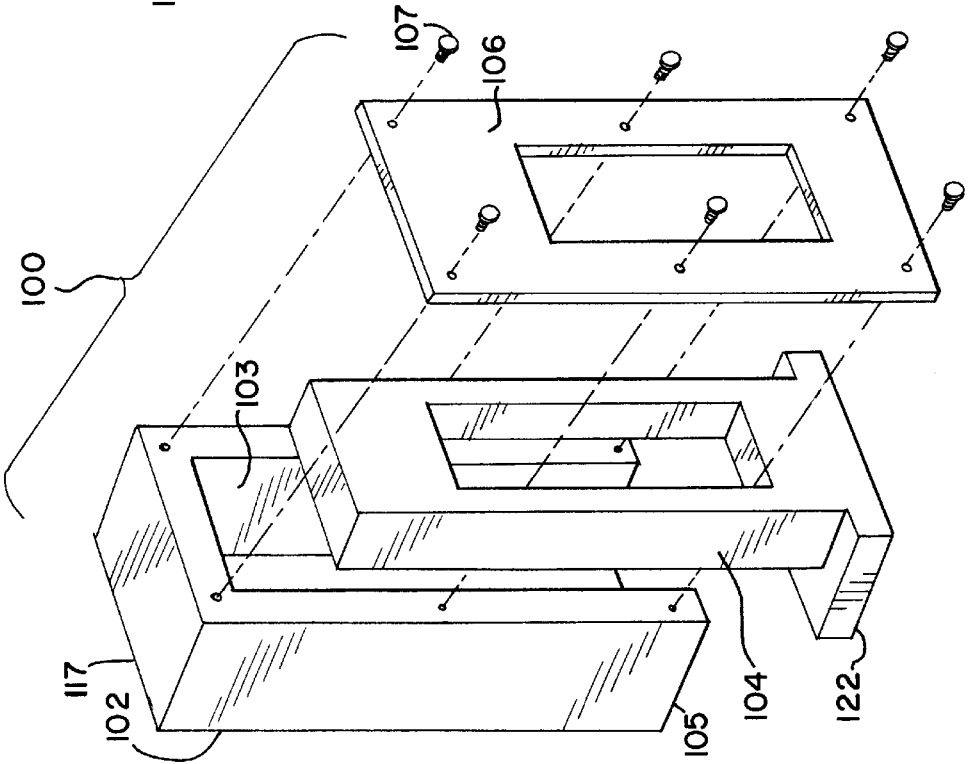
FIG. 2 is a perspective partially exploded view of one embodiment of a testing tool constructed in accordance with the principles of the present invention.

The present invention is directed to a testing tool that overcomes these disadvantages, and as illustrated in FIG. 2, the testing tool 100 includes a pair of coacting force members 102, 104 that slidably engage each other. Either member can be stationary or mobile, depending on its orientation and the work mode of the testing machine. One of the force members 102 is intended to be a stationary test member and does not move during testing. As used herein, the term "stationary" in intended to pertain the orientation of the particular force member within an overall testing machine, and in this instance, the stationary force member 102 is a member which is held stationary by a component of a testing machine in which the testing tool 100 is used.

The other force member 104 is a movable force member that slides within an internal cavity 103 that is formed within the first force member 102. This cavity 103 has a predetermined extent within the stationary force member 102 and is preferably square, or rectangular, in configuration so that its movement within the cavity 103 is generally axial movement. The cavity 103 opens at one end 105 of the first force member 102, and a cover frame 106 may be provided in order to retain the movable force member 104 within the stationary force member 102. The cover frame member is removably attached thereto with suitable means, such as screws 107. The open end 105 of the force member 102 communicates with the cavity 103 thereof and provides a passage through which the movable force member 104 may be inserted and removed. The force member 104 has a base, or stop portion 122, that projects outwardly therefrom and which is aligned with the first force member 102 and has a size and configuration sufficient to restrict the range of axial movement of the force member 104 within the stationary force member 102, whereas the cover frame 106 restricts movement of the force member 104 in a transverse direction.

Preferably, the internal cavity 103 extends generally along the majority of the length of the force block 102 and is accessible from one side 113 of the force block 102 a central opening 115 formed in the stationary force block 102 (and in the side 113). The movable force block 104 has the general approximate shape of the internal cavity 103 so that it either matingly or slidably engages the stationary force block 102. The force block 102 further has an end wall 117 that serves as a stop to limit the extent of travel of the movable force block 104 in the stationary force block 102. This end wall 117 has the same approximate size as the stop and support wall 122 of the other force block 104 so that the area at the top and bottom of the testing tool 100 is the same which results in the same distribution of forces from a testing machine in which the testing tool 100 is used.

Figure 3:
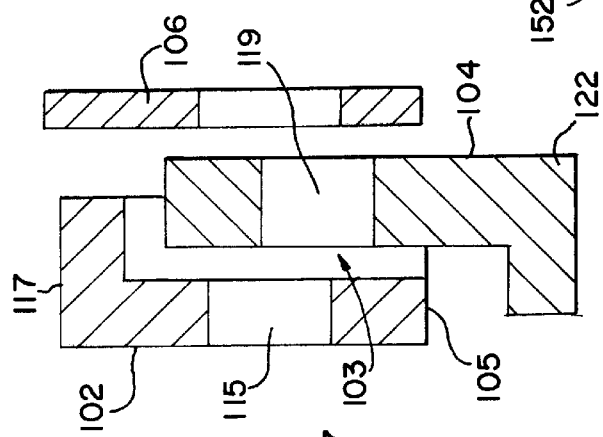
FIG. 3 is a cross-sectional, exploded view of the testing tool of FIG. 2.

As seen in FIG. 3, the stationary force block 102 is shown as having a central opening 115 that extends through the thickness of the force block 102, while the movable force block 104 has a similar central opening 119 that also extends completely through the thickness of the force block 104. These two openings 115, 119 communicate with each other, for different extents dependent upon the movement and position of the force block 104 within the outer stationary force block 102.

A second embodiment of the present invention is illustrated in FIG. 4, in which a stationary force block 150 is illustrated as having a central opening 151. In order to account for minor differences in the profile, or rectangularity, of one end 152a of the test specimen 152, a moveable member 153 in the form of a flat plate 154 is provided. This moveable member 153 has a rotatable fixture member associated therewith, and is illustrated in FIG. 4 as a rod member 155. This rod member 155 fits within a correspondingly formed socket 157 formed in the body portion 158 of the force block 150 that is disposed along a lower face 159 of the force block opening 151. The socket 157 is covered by a cover plate 160 so that the moveable member 153 may be inserted from the side of the force block 150, and the moveable member 153 may be retained in place within the force block 150. Other types of retention constructions may be used to hold the moveable member 153 in place. The movement of this member 153 may be aptly described as a rocking-type or pivoting-type or other-type of movement within the force block 150 to accommodate the edge 152a of the test specimen 152.

In the embodiment of FIG. 4, the force block 150 has been modified to fit in a tension-type testing machine. In this regard, the top face 161 of the force block 150 has a post or other vertical member 162 associated therewith. The post 162 is drilled to form a hole 163 therein, through which a pin 164 extends. The pin 164 further connects the force block 150 through the vertical post 162 to a clevis 165 so that this force block 150 may be preferably pulled along a line of action indicated by the arrow at the top of FIG. 4.

Figure 6A:
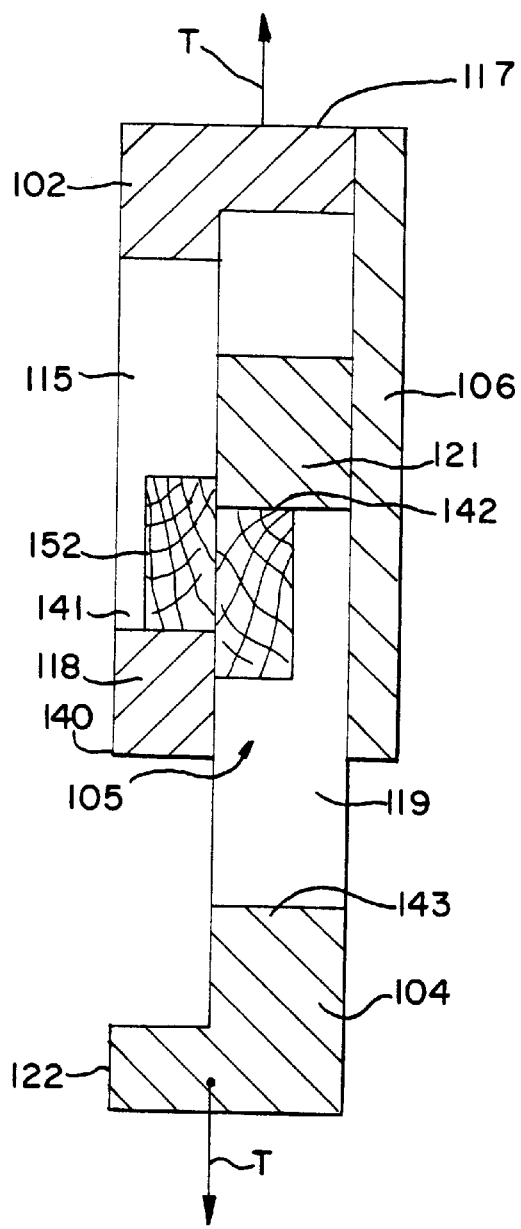
FIG. 6A is a cross-sectional elevational view of the testing tool of FIG. 2 in place within a testing machine and with a test specimen loaded thereon, illustrating the operation thereof in a tension testing mode; and, FIG. 6B is a schematic diagram of the forces exerted on the test specimen by the testing tool when in a tension mode.
Figure 6B:
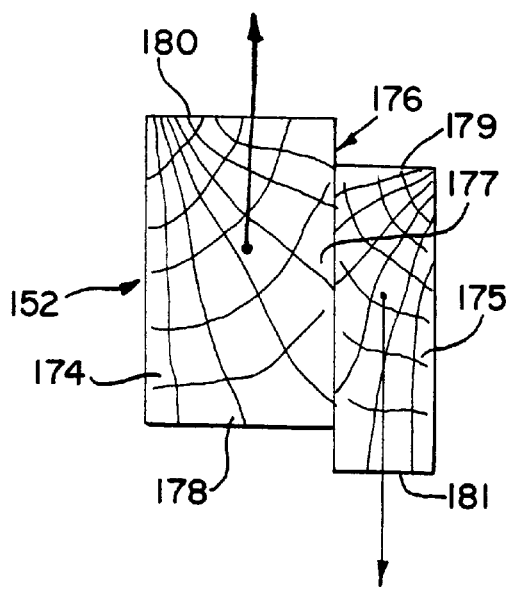

The dimensions of the top and bottom ends 117, 122 of the testing tool are important insofar as force application and transfer are concerned. As shown best in FIGS. 5A and 6A, the ends 117, 122 are large enough and are dimensioned such that any forces acting on the ends 117, 122, whether they are tension forces as shown in FIG. 6, or compressive forces as shown in FIG. 5A, effectively act through the center of the testing tool 100 and through the centers of the respective force blocks 102, 104. In this manner, as shown in the schematic diagrams of FIGS. 5B and 6B, the forces may be applied directly to the ends of the test specimens 152 in a true tension or compression mode.

Turning now to FIGS. 5B and 6B, the test specimen 152 will typically be composed of a pair of test square, or coupons, 174 & 175. An adhesive is applied to one or both of respective opposing faces 176 & 177 and the two coupons are brought together in a staggered, or offset, fashion as shown in FIGS. 5B and 6B. The test specimen 152 is then placed into the testing tool 100, through the windows or openings 115, 119 (FIGS. 5A & 6A.) so that selected opposing ends 178, 179 of the test specimen as a whole, will engage, by bearing against, the two respective force blocks 102, 104.

Where the testing machine is an Instron testing machine as indicated generally in FIG. 5A, the testing machine 200 has a pair of opposing compression heads 201, 202, one of which (typically the bottom one 202) will remain stationary, while the other one 201 will be driven toward the bottom head by a controlled driver, such as a hydraulic mechanism (not shown). In this mode of operation, the two force blocks 102, 104 are pushed toward each other by the testing machine 200, and the resultant forces exerted on the two force blocks 102, 104 will be transmitted roughly down the centers of the force blocks 102, 104. For precise measurements, the pivot member can be installed on the surface of 143 and a linkage between block 102 and the compression head on the moving beam. This linkage not only improves the working efficiency by lifting the block member 102 mechanically, but also eliminates the reading error accompanied with the shear tool in ASTM D 905. As discussed above, that error resulted from the weight of the blade 25 in FIGS. 1A and B.

Each of the two force blocks 102, 104 has a plurality of force-imposing bearing surfaces defined thereon. Each force block has at least two distinct surfaces, which contribute to the present invention's ability to be used equally in both compression and tension mode testing. This is best illustrated in FIGS. 5A and 6A as set forth in greater detail below. FIG. 5A which shows the shear testing device 100 in operation when compressive forces C are to the testing tool 100 and the test specimen 152 contained therein. These force-imposing surfaces 140–143 are split into pairs of surfaces. One pair 140, 141 is associated with the force block 102, while the other pair 142, 143 is associated with force block 104. The latter pair of surfaces 142, 143 are disposed on opposite internal faces of the internal opening 119 of the force block 104, while the former pair of surfaces 140, 141 are disposed on opposite sides of the bottom wall member 118 of the force block 102.

Returning to FIG. 6A, the testing tool 100 is shown in a tension mode of operation wherein tension forces T are applied to the opposite ends 117, 122 of the testing tool, such as by an arrangement similar to that shown in FIG. 4. The imposition of these tension forces cause a like imposition of tension forces on the test specimen 152, as shown in detail in FIG. 6B. The forces are transmitted along the reaction or engagement surfaces 178, 179 of the test specimen 152, which are opposite ends of the two test coupons 174, 175. One edge 178 engages the inner face of the central opening 115 of the force block 102, while the other edge 179 engages the top inner face of the top end 121 of force block 104.

A similar, but reversed arrangement of forces occurs in the testing tool for operation in a compression mode. Returning to FIG. 5A, it can be seen that the test specimen 152 is placed within the opening 119 of the force block 104 so that its opposing edges 180, 181 abuttingly engage the respective surfaces 140 and 143 of the force blocks 102, 104, respectively. Now the bottom surface 140 of the force block 102 is used to impose a force on the test specimen 152, while the surface 143 of the opening 119 of the force block 104 is used to impose the counteracting force on the test specimen 152. The present invention, by its structure, permits the even application of force couples on test specimens, thereby decreasing the likelihood of unbalanced forces and inaccurate test results being obtained. Similarly, the use of the pivot member 153 as shown in FIG. 4 will likewise decrease the possibility of inaccurate testing.

It will be appreciated that the embodiments of the present invention which have been discussed are merely illustrative of few of the applications of the principles of the invention. Numerous modifications may be made by those skilled in the art without departing from the spirit and the scope of the invention.

What is claimed is:

1. A testing tool adapter for use with an Instron testing machine, the testing machine having two opposing work heads, the testing tool adapter is suitable for testing the shear strength in adhesives, test specimens include first and second test blocks which have an adhesive applied to an interface of the first and second test blocks, the test blocks being offset such that a first end of said first test block projects past a second body portion of the second test block and a second end of said second test block projects past a first body portion of said first test block, such that said test specimen, has a pair of opposing edges that lie upon said first and second test block first ends, the testing tool adapter comprising:

first and second force blocks, said first force block having a base portion and a vertical body portion extending upwards, said vertical body portion having a first cavity formed therein for receiving the second test block therein, said first force block further including a first opening formed in said vertical body portion for receiving one of said first and second test blocks therein;

said second force block slidably engaging said first force block, said second force block having a vertically depending body portion and a horizontally extending base portion, said vertically depending body portion being at least partially received within said first force block cavity, said first and second force blocks relatively moveable;

said second force block including a second opening disposed in said vertically depending body portion thereof, said second opening sized to receive at least the other of said first and second test blocks therein, said second force block having a reaction surface for engaging said other test block, said second force block reaction surface facing a second direction that is opposite in direction to said first force block reaction surface; and, a cover member engaging said first force block and retaining said second force block in slidable engagement with said first force block.

2. The testing tool adapter according to claim 1, further including a moveable member engaging said second force block within said second opening thereof, the moveable member defining said second force block reaction surface.

3. The testing tool adapter according to claim 2, wherein said moveable member is a rocking member having a stem portion that is received within an opening of said second force block.

4. The testing tool adapter according to claim 1, wherein said first and second force block base portions are approximately the same size.

5. The testing tool adapter according to claim 1, wherein said first and second force block base portions have respective planar contact surfaces for engaging the Instron testing machine work heads and operating in a compression test mode.

6. The testing tool adapter according to claim 1, wherein said first and second force block base portions include means for engaging opposing work heads of the Instron testing machine when operated in a tension mode. a tension mode.

7. The testing tool adapter according to claim 6, wherein said engagement means includes at least one post formed on one of said first and second force block base portions, the post having a clevis operatively connected thereto for connection to one of the Instron testing machine work heads.

8. The testing tool adapter according to claim 6, wherein said engagement means includes at least one post formed on one of said first and second force block base portions, said post having a socket operatively connected thereto connection to one of the Instron testing machine work heads.

9. The testing tool adapter according to claim 1, wherein said cover member also includes an opening formed therein dimensioned to said second force block second opening.

10. The testing tool adapter according to claim 1, wherein said base portion of each of said first and second force blocks is wider than said respective body portions thereof.

11. The testing tool adapter according to claim 1, wherein said first force block has a general U-shaped configuration and said first force block cavity has a depth a thickness of said second force block body portion.

12. A testing tool adapter for use with a shear strength testing machine that is used to determine the shear strength of adhesives by testing a test specimen formed from two test coupons adhered together with an adhesive, comprising:

first and second force blocks slidably engaged, said first force block having a body portion of predetermined length and a cavity formed therein having a predetermined length and depth, said second force block slidably disposed within said first force block, said second force block having a body portion with a thickness of said first force block cavity depth, said second force block body portion having a length of said first force block cavity length, said first and second force blocks having respective first and second openings for cooperatively receiving said test specimen therein and which communicate when said first and second force blocks are slidably engaged, said first and second force blocks disposed offset when a test specimen is disposed within said first and second openings, said first and second force blocks further including respective reaction surfaces for engaging said ends of said test specimen such that said test specimen is adapted for shear strength testing in a tension testing mode and a compression testing mode.

13. The testing tool adapter of claim 12, further including a cover member that retains said second force block in place within said first force block and restricts said second force block from transverse movement.

14. The testing tool adapter of claim 12, wherein at least one of said first and second force blocks include means for stopping relative axial movement between said first and second force blocks.

15. A testing tool adapter for use in a testing machine for testing an adhesive for resistance to shear forces of an adhesive, the adhesive being applied along a common face that extends between two test coupons to form a test specimen, the testing tool adapter comprising:

first and second coacting force blocks, said first coacting force block slidably engaging said second coacting force block, each of the two coacting force blocks having a central opening formed therein such that when said coacting force blocks are relatively moved, said coacting force block openings communicate with each other to define a central widow adapted to receive said test specimen may be placed by an operator of said testing tool, said first coacting force block having a base portion for engagement with one end of said testing machine and said second coacting force block having a base portion for engagement with another end of said testing machine, one of said first and second coacting force blocks disposed within a cavity formed within the other of said first and second coacting force blocks, whereby movement of said first and second coacting force blocks causes offset movement exposing opposing reaction surfaces on said first and second coacting force blocks which engage opposite ends of said test specimen.

* * * * *